(12) United States Patent
Cohen et al.

(10) Patent No.: US 8,851,068 B2
(45) Date of Patent: Oct. 7, 2014

(54) PERSONAL INHALATION DEVICES

(75) Inventors: Scott A. Cohen, Portland, ME (US); Michael J. Bedecs, Jupiter, FL (US)

(73) Assignee: AJ Marketing LLC, Portland, ME (US)

( * ) Notice: Subject to any disclaimer, the term of this patent is extended or adjusted under 35 U.S.C. 154(b) by 646 days.

(21) Appl. No.: 12/869,000

(22) Filed: Aug. 26, 2010

(65) Prior Publication Data

US 2011/0036346 A1 Feb. 17, 2011

Related U.S. Application Data

(63) Continuation-in-part of application No. 29/335,784, filed on Apr. 21, 2009, now abandoned, and a continuation-in-part of application No. 29/335,785, filed on Apr. 21, 2009, now abandoned, and a continuation-in-part of application No. 29/335,786, filed on Apr. 22, 2009, now abandoned.

(51) Int. Cl.
| | |
|---|---|
| A61M 15/06 | (2006.01) |
| A61M 16/00 | (2006.01) |
| A61M 11/00 | (2006.01) |
| A61M 11/04 | (2006.01) |
| A61M 15/00 | (2006.01) |

(52) U.S. Cl.
CPC ....... *A61M 15/06* (2013.01); *A61M 2205/3306* (2013.01); *A61M 2205/502* (2013.01); *A61M 2205/123* (2013.01); *A61M 2205/3368* (2013.01); *A61M 2202/0468* (2013.01); *A61M 2205/587* (2013.01); *A61M 11/042* (2013.01); *A61M 2016/0024* (2013.01); *A61M 15/0085* (2013.01); *A61M 15/0065* (2013.01); *A61M 2205/8206* (2013.01); *A61M 2205/581* (2013.01)
USPC ............ 128/202.21; 128/200.14; 128/203.27

(58) Field of Classification Search
CPC ....... A24F 13/06; A24F 13/02; A24F 47/002; A61M 2202/064; A61M 16/18
USPC ............ 128/202.21, 200.11–200.16, 203.15, 128/204.13, 203.23, 203.25–203.27, 128/204.14, 204.17, 204.22; 604/186; 131/270–273
See application file for complete search history.

(56) References Cited

U.S. PATENT DOCUMENTS

| | | | | |
|---|---|---|---|---|
| 4,520,451 | A | * | 5/1985 | McLaughlin ................. 700/236 |
| 5,899,204 | A | * | 5/1999 | Cochran .................. 128/205.23 |
| 6,102,036 | A | * | 8/2000 | Slutsky et al. ........... 128/203.15 |
| 6,443,146 | B1 | * | 9/2002 | Voges ....................... 128/200.14 |
| 6,684,880 | B2 | * | 2/2004 | Trueba ...................... 128/200.16 |
| 6,772,756 | B2 | * | 8/2004 | Shayan ..................... 128/203.26 |
| 7,131,599 | B2 | * | 11/2006 | Katase ........................ 239/102.1 |
| 7,617,821 | B2 | * | 11/2009 | Hughes .................... 128/200.24 |
| 2004/0233668 | A1 | * | 11/2004 | Telfer et al. ................... 362/252 |

(Continued)

FOREIGN PATENT DOCUMENTS

CN 201213951 Y 4/2009

*Primary Examiner* — Melanie Hand
*Assistant Examiner* — Ned T Heffner
(74) *Attorney, Agent, or Firm* — Preti Flaherty Beliveau & Pachios LLP (57) ABSTRACT

A personal inhalation device includes an outer shell having an orifice formed therein and containing a medium having one or more deliverables and an atomizing unit disposed within the shell. The atomizing unit atomizes the medium when a user puffs on the orifice such that vapor containing the deliverables is discharged through the orifice. The personal inhalation device is further capable of metering the deliverables discharged with the vapor.

18 Claims, 6 Drawing Sheets

(56) References Cited

U.S. PATENT DOCUMENTS

2006/0196505 A1* 9/2006 Izuchukwu ............ 128/203.15
2006/0196518 A1 9/2006 Hon
2007/0267031 A1 11/2007 Hon
2009/0126745 A1 5/2009 Hon

* cited by examiner

PERSONAL INHALATION DEVICES

CROSS REFERENCES TO RELATED APPLICATIONS

This application is a Continuation-In-Part of copending U.S. patent application Ser. No. 29/335,784, filed Apr. 21, 2009, copending U.S. patent application Ser. No. 29/335,785, filed Apr. 21, 2009, and copending U.S. patent application Ser. No. 29/335,786, filed Apr. 22, 2009, all of which are hereby incorporated by reference.

BACKGROUND OF THE INVENTION

This invention relates generally to inhalation devices and more particularly to personal inhalation devices having regulated operation.

The term "personal inhalation device" refers to a device that delivers doses of one or more substances, chemicals, medicines, ingredients or the like (hereinafter referred to as "deliverables") by way of inhaled vapor. Generally, a personal inhalation device holds a medium (such as a solution) that contains the deliverable and is atomized when a user draws or puffs on the device, thereby creating a vapor containing the deliverable. The vapor and the deliverable are inhaled by the user. For the sake of clarity, as used herein, the term "inhale" refers to a person drawing in a substance (typically via the mouth but could also be via the nose, a tracheostomy, or the like) and can include, but does not necessarily require, the substance entering the lungs. As used herein, the term "vapor" refers to both a substance in the gaseous state and a suspension of finely divided solid particles or liquid droplets in a gas, including aerosols, mists and the like.

While a wide variety of deliverables are possible, personal inhalation devices are often used to deliver nicotine by inhalation, and when so used are sometimes referred to as an "electronic cigarette" or "e-cigarette." Such devices provide several advantages as an alternative to smoked tobacco products. Inhaling a vapor containing nicotine is believed to preclude the tar and other harmful effects of traditional tobacco smoke. Also, the vapor, which dissipates quickly, reduces the hazards of secondhand smoke or passive smoking among bystanders. And because there is no actual combustion involved, personal inhalation devices avoid the fire hazard and environmental problems associated with tobacco smoking. Personal inhalation devices also have an advantage with respect to other alternative nicotine delivery systems (e.g., nicotine chewing gum, nicotine patches, etc.) in that inhaling the vapor can produce a flavor and physical sensation similar to that of inhaled tobacco smoke.

Despite these advantages, some regulatory agencies have questioned using personal inhalation devices to deliver nicotine, particularly raising concerns about the uncontrolled and inconsistent amounts of nicotine delivered by such devices. Some jurisdictions around the world have placed limits on—or even banned—the use of electronic cigarettes. In the United States, the sale and use of personal inhalation devices might require approval of the Food and Drug Administration.

Accordingly, it is desirable to provide a personal inhalation device that is more likely to gain regulatory approval.

SUMMARY OF THE INVENTION

A personal inhalation device including an outer shell having an orifice formed therein and containing a medium having one or more deliverables and an atomizing unit disposed within the shell. The atomizing unit atomizes the medium when a user puffs on the orifice such that vapor containing the deliverables is discharged through the orifice. The personal inhalation device is further capable of metering the deliverables discharged with the vapor.

DETAILED DESCRIPTION OF THE INVENTION

Figure 1:
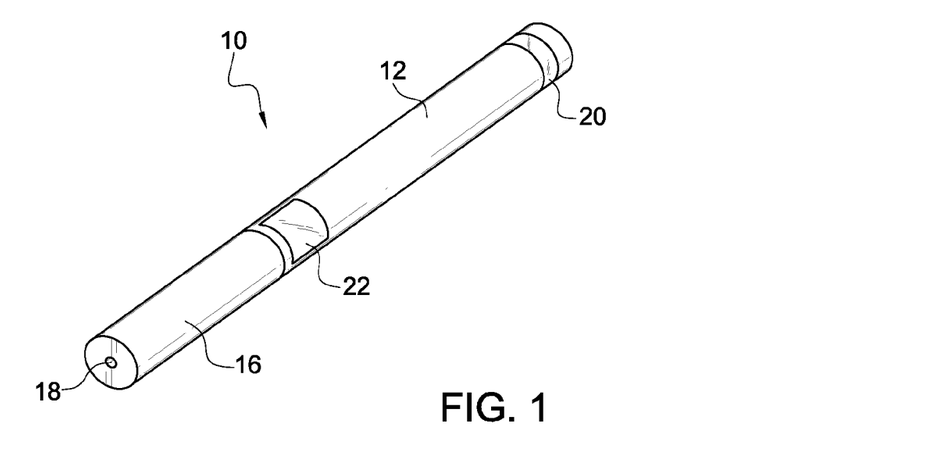
FIG. 1 perspective view of one embodiment of a regulated personal inhalation device.
Figure 2:
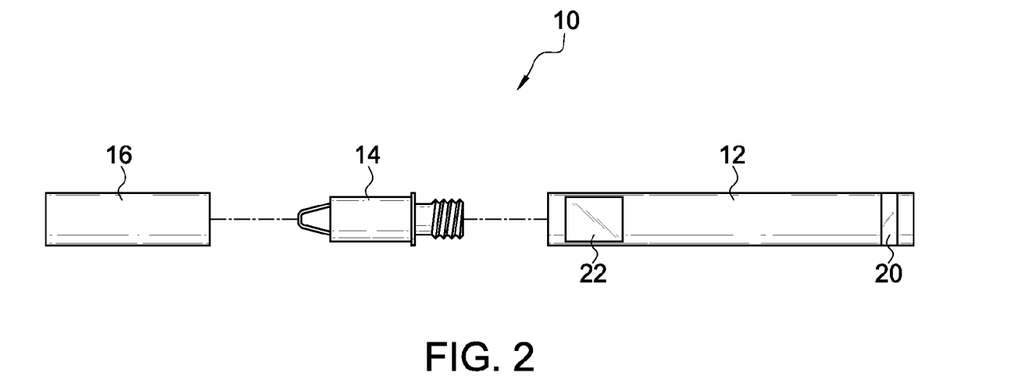
FIG. 2 is an exploded view of the regulated personal inhalation device of FIG. 1.

Referring to the drawings wherein identical reference numerals denote the same elements throughout the various views, FIGS. 1 and 2 show one embodiment of a regulated personal inhalation device 10. In this embodiment, the personal inhalation device 10 is constructed to resemble a cigarette in appearance, but it should be noted that the present invention can be constructed to resemble various other items, including but not limited to a cigar or a pipe. In addition, the present invention can be provided with a construction that does not resemble any particular item.

The personal inhalation device 10 includes three principal components: an electronics section 12, an atomizing unit 14 and a cartridge 16. In the illustrated embodiment, the electronics section 12 is connected to one end of the atomizing unit 14 by means of a screw-on connection, and the cartridge 16 is connected to the other end of the atomizing unit 14 by an interference fit (sometimes referred to as a friction fit). When so assembled, the personal inhalation device 10 defines an elongated, cylindrical shape having a length-to-diameter ratio that is similar to the length-to-diameter ratio of a standard cigarette. As described in more detail below, the cartridge 16 stores a deliverable-containing medium which is atomized in the atomizing unit 14 when a user draws or puffs on the cartridge end of the inhalation device 10. As used herein, "drawing" or "puffing" on the inhalation device 10 involves a user placing the cartridge end of the inhalation device 10 into the mouth and sucking in, thereby drawing air through the inhalation device 10. This creates a vapor that is inhaled by the user through an orifice 18 formed in the end of the cartridge 16. An indicator light 20 at the other end of the electronics section 12 will illuminate when the user inhales vapor from the inhalation device 10, and a display 22 is mounted on the exterior surface of the electronics section 12 for outputting additional information to the user. The operation of the inhalation device 10 is controlled by micro-electronic components (hereinafter referred to as the "control electronics") contained in the electronics section 12.

Instead of a separable interference fit, the atomizing unit 14 and the cartridge 16 could be joined together in a fixed manner, such as by gluing or the like. In this instance, the combined atomizing unit-cartridge component would by disposable, and replaced after a certain number of uses or when the medium in the cartridge is deplete.

Figure 3:
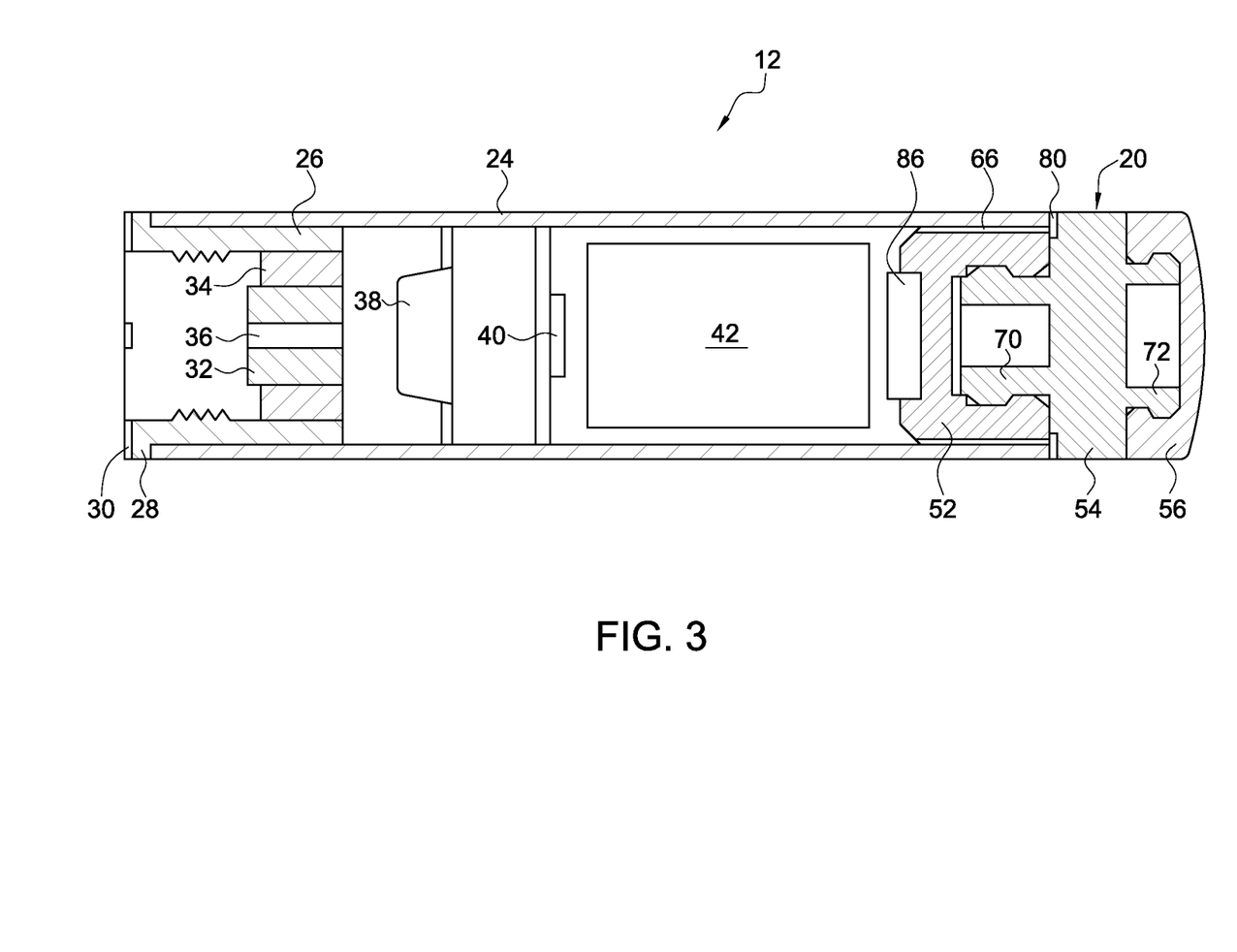
FIG. 3 is a cross-sectional view of a portion of the regulated personal inhalation device of FIG. 1.

Referring to FIG. 3, the electronics section 12 includes a first cylindrical housing 24 that is open at both ends. A first coupling 26, having internal screw threads, is mounted in a first end of the first housing 24. The first coupling 26 comprises a cylindrical body that fits snuggly inside the first housing 24 (thereby creating an interference fit between these components) and has a flange 28 on a first end thereof that abuts the end of the first housing 24. A number of slots 30 are formed in the flange 28 to create air passages into the interior of the first coupling 26. The internal threads are formed on the inner surface of the cylindrical body, near the first end. A first electrical contact 32 is mounted inside the cylindrical body of the first coupling 26, adjacent to the second end thereof, by means of a first insulating sleeve 34. The first electrical contact 32 is made of an electrically conductive material and comprises a substantially cylindrical member having a central bore 36 formed therethrough along its longitudinal axis. The cylindrical body of the first coupling 26 is also made of an electrically conductive material. The first insulating sleeve 34 is made of a non-electrically conductive material.

Figure 4:
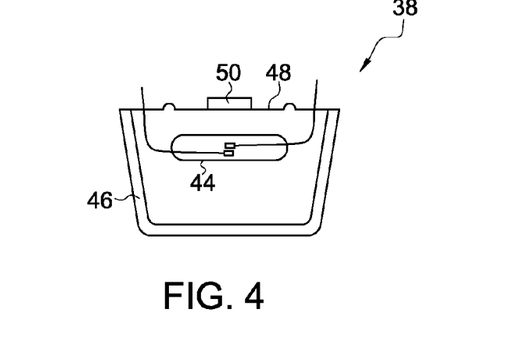
FIG. 4 is a cross-sectional view of one embodiment of a pressure transducer used in the regulated personal inhalation device of FIG. 1.

The first cylindrical housing 24 further contains a pressure transducer 38, an electronic circuit board 40, and a power source 42. Each of these components is mounted within the first housing 24 so as to allow air to freely flow around or past the component. Also, the pressure transducer 38 and the electronic circuit board 40, as well as the first coupling 26 and the first electrical contact 32, are electrically connected to the power source 42 in any suitable manner, such as wiring (not shown). The pressure transducer 38 is designed to react to a pressure increase due to air flowing through the first housing 24 to actuate the control electronics on the electronic circuit board 40 and other electric components of the inhalation device 10. In one possible embodiment, shown in FIG. 4, the pressure transducer 38 can comprise a reed switch 44 disposed in a casing 46, which is covered by a flexible member 48. A magnet 50 is mounted on the flexible member 48. These elements are arranged such that a flow of air through the first housing 24 will deflect the flexible member 48 and thereby move the magnet 50 closer to the reed switch 44. The magnet's magnetic field then closes the reed switch 44, which completes a circuit between the power source 42 and the electronic circuit board 40. When the flow of air ceases, the flexible member 48 and the magnet 50 return to their normal positions, and the reed switch 44 re-opens. The power source 42 can be a battery or any other suitable energy storage device, such as a capacitance-based device. The electronic circuit board 40 contains control electronics for controlling operation of the inhalation device 10.

Figure 5:
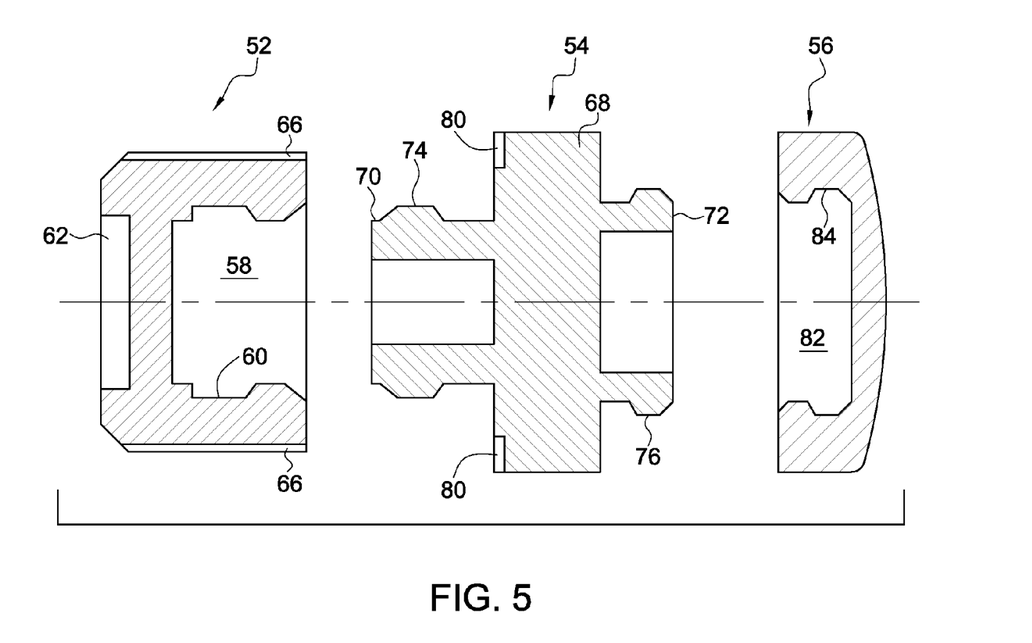
FIG. 5 is an exploded, cross-sectional view of a light assembly used in the regulated personal inhalation device of FIG. 1.
Figure 6:
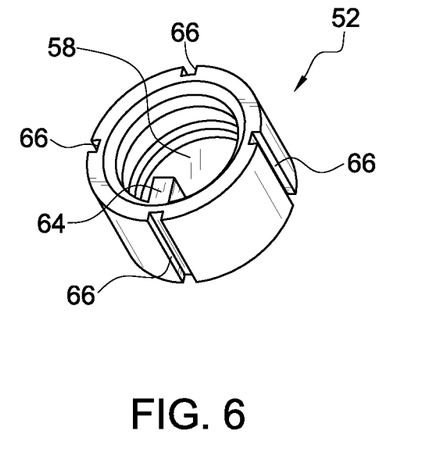
FIG. 6 is a perspective view of a base member from the light assembly.
Figure 7:
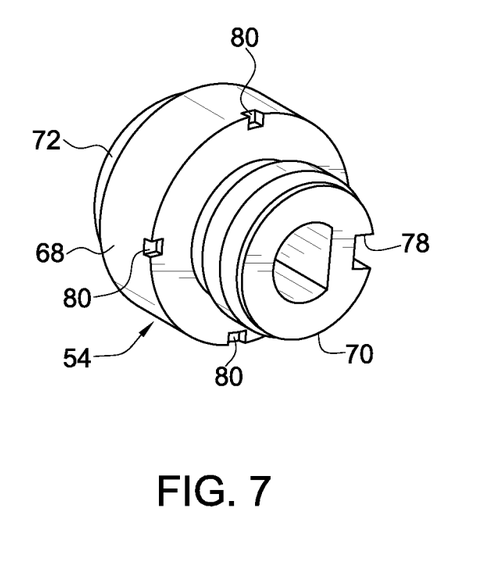
FIG. 7 is a perspective view of a lens member from the light assembly.

Referring again to FIG. 3, as well as FIGS. 5-7, the indicator light 20 is an assembly comprising a base member 52, a lens member 54, and a tip member 56. The base member 52 is a substantially cylindrical piece of a translucent material that is mounted in the first housing 24 with one end being positioned substantially flush with the second end of the first housing 24. The outside diameter of the base member 52 closely matches the inside diameter of the first housing 24 so that the base member 52 is held inside the first housing 24 by an interference fit. A circular cavity or socket 58 is formed in this end of the base member 52, and an annular groove 60 is formed in the inner surface of the socket 58. A relatively shallow recess 62 is provided in the opposite end of the base member 52. As best seen in FIG. 6, an axially extending rib 64 is formed on the inner surface of the socket 58. Several axially extending channels 66 are provided in the outer cylindrical surface of the base member 52. These channels 66 extend the length of the base member 52 and function as air passages.

The lens member 54 is a unitary piece made of a translucent material, which can be colored. The lens member 54 comprises a cylindrical body portion 68 having an outside diameter that is substantially equal to the outside diameter of the first housing 24. A first connector 70 extends from one end of the body portion 68 and a second connector 72 extends from the other end of the body portion 68. The first connector 70 is an annular projection having a first retaining lip 74 formed on its outer cylindrical surface. Similarly, the second connector 72 is an annular projection having a second retaining lip 76 formed on its outer cylindrical surface. As best seen in FIG. 7, an axially extending slot 78 is provided in the outer surface of the first connector 70. A number of small notches 80 are formed in the first end of the body portion 68, at the outer cylindrical surface. When assembled, the first connector 70 is inserted into the socket 58, with the first retaining lip 74 being received in the groove 60 to axially retain the first connector 70 in the socket 58. Furthermore, the rib 64 is received in the slot 78, thereby preventing relative rotational movement between the lens member 54 and the base member 52. Also, each notch 80 aligns with a corresponding one of the channels 66 to define a passage for external air to flow into the interior of the first housing 24.

The tip member 56 is a disc-shaped member made of an opaque material and having an outside diameter that is substantially equal to the outside diameter of the cylindrical body portion 68 of the lens member 54. One end of the tip member 56 defines a closed, curved surface, and the other end has a circular cavity 82 with an annular groove 84 formed in the inner surface thereof. When assembled, the second connector 72 is inserted into the cavity 82, with the second retaining lip 76 being received in the groove 84 to axially retain the tip member 56 on the second connector 72.

The indicator light 20 further includes a light source 86 that is mounted in the shallow recess 62 of the base member 52. The light source 86, which can be any suitable type of light source, such as a light emitting diode or the like, is electrically connected to the power source 42 and the circuit board 40 and is activated at the desired times by the control electronics. When the light source 86 is activated, the translucent base member 52 functions as a light pipe and transmits the light to the lens member 54. The light is then transmitted through the translucent lens member 54, causing the outer cylindrical surface of the body portion 68 (which is visible to the user while inhaling on the inhalation device 10) to be illuminated.

Figure 8:
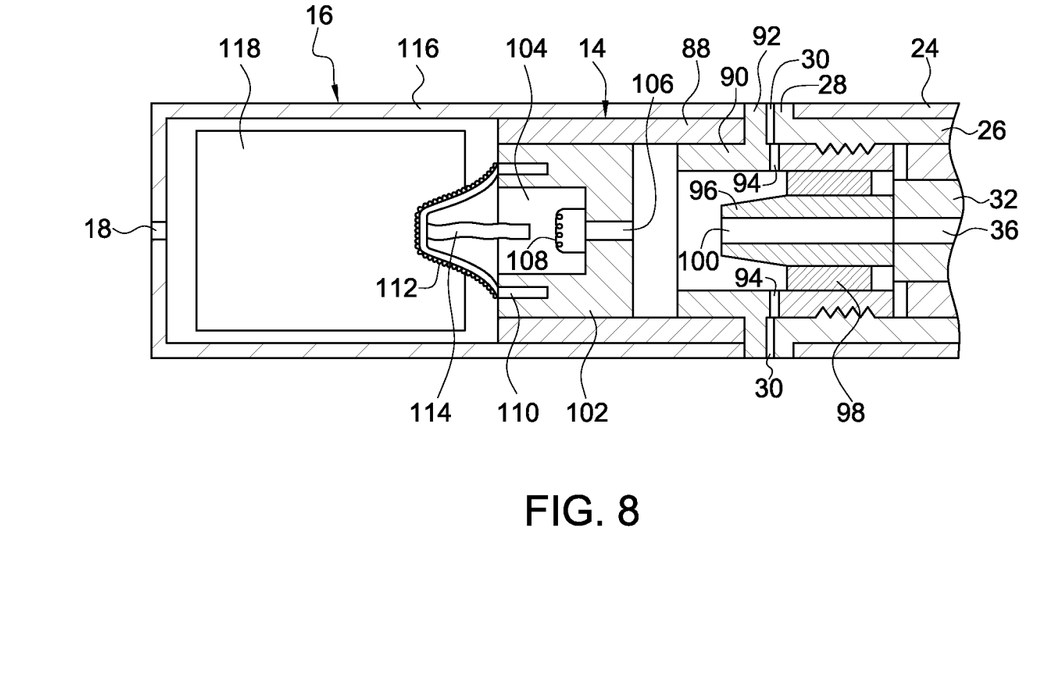
FIG. 8 is a cross-sectional view of another portion of the regulated personal inhalation device of FIG. 1.

Referring to FIG. 8, the atomizing unit 14 includes a second cylindrical housing 88 that is open at both ends. A second coupling 90, having external screw threads, is mounted in a first end of the second housing 88. The second coupling 90 includes a cylindrical body having an annular flange 92 formed on its outer surface, spaced a short distance from a first end thereof. The first end of the second coupling 90 is inserted into the second housing 88 so that the annular flange 92 abuts the first end of the second housing 88. The outside diameter of the coupling body closely matches the inside diameter of the second housing 88 so that the second coupling 90 is held in the second housing 88 by an interference fit. Radial holes 94 extend through the cylindrical body of the second coupling 90 and create air passages into the interior of the second coupling 90. The external threads are formed on the outer surface of the cylindrical body, near the second end thereof, and mesh with the internal threads of the first coupling 26 so as to join the atomizing unit 14 to the electronics section 12 via a screw-on connection. A second electrical contact 96 is mounted inside the cylindrical body of the second coupling 90 by means of a second insulating sleeve 98. The second electrical contact 96 is made of an electrically conductive material and comprises a substantially cylindrical member having a central bore 100 formed therethrough along its longitudinal axis. The cylindrical body of the second coupling 90 is also made of an electrically conductive material. The second insulating sleeve 98 is made of a non-electrically conductive material, such as plastic.

A holder 102 is disposed in the second housing 88, with one end thereof flush with the second end of the second housing 88. The holder 102 comprises a cylindrical body, made of a non-electrically conductive material, retained in the second housing 88 by an interference fit. A cavity formed in a first end of the holder 102 defines an atomization chamber 104. An air passage 106 extends through the holder 102, along its longitudinal axis, from the atomization chamber 104 to the second end of the holder 102. An atomizing device 108 is mounted in the atomization chamber 104 and is electrically connected to the second coupling 90 and the second electrical contact 96 in any suitable manner, such as wiring (not shown). In the illustrated embodiment, the atomizing device 108 is a heating coil positioned adjacent to the air passage 106. Alternatively, the atomizing device 108 could be another type of device, such as an ultrasonic atomizer. A yoke-shaped strut 110 is mounted on the first end of the holder 102, straddling the atomization chamber 104. The portion of the strut 110 extending away from the holder 102 supports a metal mesh 112. A wick 114 supported by the strut 110 extends into the atomization chamber 104.

The cartridge 16 includes a third cylindrical housing 116 that is open at a first end and closed at a second end, with the orifice 18 being formed in the closed second end. The open first end of the cartridge 16 fits tightly over the second housing 88 and is held thereon by an interference fit. A reservoir 118 is mounted in the cartridge 16 in such a manner so as to allow air to flow around the reservoir 118 to the orifice 18. The reservoir 118 contains the medium that is atomized in the atomization chamber 104 when a user draws or puffs on the inhalation device 10.

The medium can be in the form of a solution comprising any desired solute dissolved in a suitable solvent such as water, propylene glycol, or the like. The solute can be one or more substances that provide the deliverable or deliverables to be delivered with the vapor inhaled by the user. The medium can comprise other forms such as gels and powders. In the illustrated embodiment, the medium is a liquid solution, and the reservoir 118 can comprise an adsorbent pad that holds the solution. Possible deliverables include nicotine, caffeine, medications, and vitamins. Using nicotine as an deliverable allows for the delivery of nicotine without the tar and other harmful effects of traditional smoking of tobacco. Another possible deliverable is tetrahydrocannabinol (THC), the primary psychoactive substance in marijuana, for use in jurisdictions in which medical marijuana is permitted. The deliverables could also comprise flavorings, such as menthol, fruit flavors, etc., that have no particular chemical effects other than taste.

The electronics section 12 and the atomizing unit 14 are joined with a screw-on connection, as described above. When these components are so joined, the first and third cylindrical housings 24, 116 define an outer shell of the inhalation device 10. Furthermore, the flange 28 of the first coupling 26 abuts the annular flange 92 of the second coupling 90, and the first and second electrical contacts 32, 96 contact one another. Being electrically conductive, these elements create an electric circuit that conducts power from the power source 42 to the atomizing device 108, which is controlled by the electronics. When the cartridge 16 is mounted on the atomizing unit 14, the strut 110 and metal mesh 112 engage the reservoir 118, allowing media (e.g., solution) to be wicked through the mesh 112 and onto the wick 114. The outer shell of the illustrated embodiment is cylindrical such that the personal inhalation device 10 resembles a cigarette in appearance. However, the personal inhalation device 10 is not limited to a cylindrical outer shell; the personal inhalation device 10 can take on different shapes and configurations, as noted above.

In operation, a user inhales vapor from the inhalation device 10 by puffing on the orifice 18 in the cartridge end. This causes external air to be drawn into the inhalation device 10. Specifically, air is drawn in through the slots 30 and then passes through the holes 94 into the interior of the second coupling 90. Air is also drawn in through the notches 80 and passes through the axial channels 66 into the interior of the first housing 24. The air flowing through the first housing 24 triggers the pressure transducer 38, thereby activating the control electronics, which power the light source 86 and the atomizing device 108. The air in the first housing 24 flows through the bores 36, 100 of the first and second electrical contacts 32, 96, respectively, and joins the air that has entered via the slots 30 and the holes 94. The combined air flow then passes through the air passage 106 into the atomization chamber 104. The air is heated as it flows over the atomizing heating coil 108. The heated air then passes over the wick 114 causing the medium that has been absorbed into the wick 114 to be atomized, creating a vapor containing the deliverables from the medium. The vapor flows around the reservoir 118, and is discharged through the orifice 18 into the user's mouth. Each instance of the user drawing or puffing on the inhalation device 10 is referred to herein as a "puff."

Figure 9:
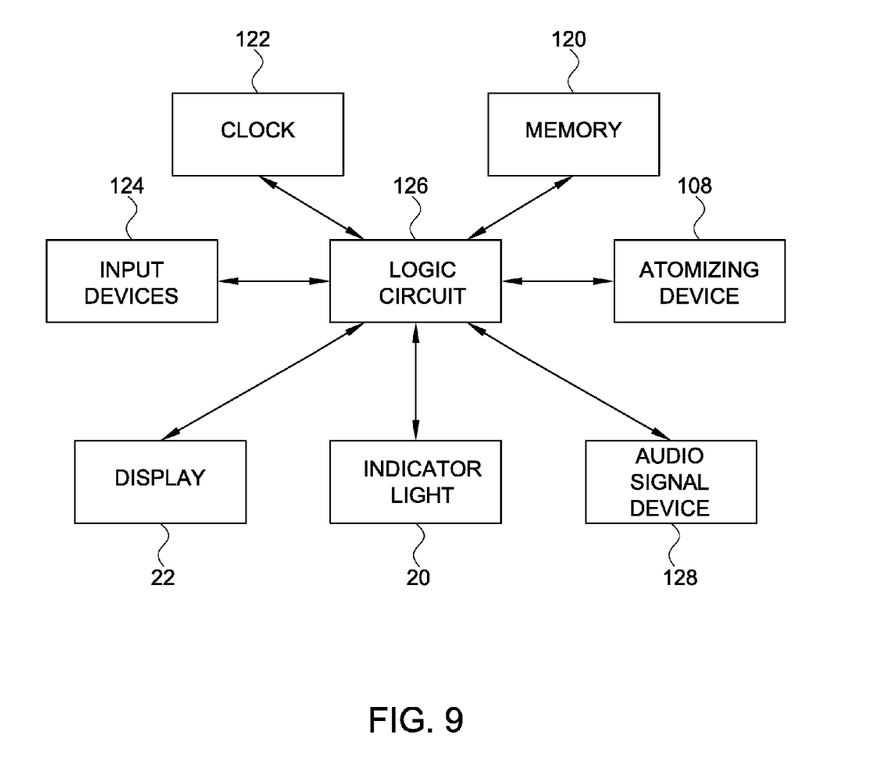
FIG. 9 is a schematic view depicting one embodiment of control electronics for the regulated personal inhalation device of FIG. 1.

As mentioned above, the electronic circuit board 40 contains control electronics for controlling operation of the regulated personal inhalation device 10. Referring to FIG. 9, one possible embodiment of the control electronics comprises a memory 120 and a clock 122 connected to a logic circuit 126. The logic circuit 126 is also connected to one or more input devices 124, as well as the atomizing device 108, the indicator light 20, and the display 22. An audio signal device 128, such as a buzzer, can also be connected to the logic circuit 126. The indicator light 20, the display 22, and the audio signal device 128 are controlled by the logic circuit 126 to provide feedback to the user.

The control electronics are programmable such that a user is able to selectively determine the operation of the inhalation device 10. The one or more input devices 124 provide a user interface for programming the control electronics, allowing the user to select an operating mode, turn metering (described below) on and off, vary metering, and otherwise set or change operating parameters of the inhalation device 10. Programming instructions can be either embedded in the logic circuit 126 or stored in the memory 120, with the desired programming being called up for use by the logic circuit 126 via manipulation of one or more of the input devices 124. Programming instructions also can be uploaded from an external device via one or more of the input devices 124, or accessed directly from an input device.

Some possible means and techniques for programming the control electronics include, but are not limited to, the following examples. One example uses an input device in the form of a pin inserted into a receptacle formed in the inhalation device 10. Typically, a series of pins is provided, with each pin having a means (such as a resistive circuit or mechanical features similar to the teeth on a key) defining unique programming instructions. The receptacle makes a circuit connection with the logic circuit 126 such that the programming instructions are provided to the logic circuit 126. The pin defining the desired programming instructions is inserted into the receptacle in order to produce the desired programming of the control electronics.

In another example, the inhalation device 10 has an input device in the form of a button or switch electrically connected to the logic circuit 126. The button or switch is mounted on the inhalation device 10 in a manner accessible to the user so that the user can press the button or switch. Programming instructions are entered by pressing the button or switch in a predetermined sequence. Different sequences are provided for the various programming instructions; the user inputs the appropriate sequence to produce the desired programming. Other possibilities involve using the pressure transducer 38 as an input device. For instance, the user could trigger the pressure transducer 38 by sequentially inhaling and/or exhaling through the orifice 18 in various patterns or combinations. The desired programming is achieved through the appropriate sequence of inhalations and/or exhalations. Alternatively, the pressure transducer 38 could be triggered by sequentially tapping the inhalation device 10 against a surface (or tapping on the inhalation device 10), whereby each tap would cause the reed switch 44 to close. In this case, the desired programming is achieved through a particular sequence of taps. It is also possible to use an input device in the form of an accelerometer disposed inside in the inhalation device 10, whereby shaking or tapping the inhalation device 10 activates the accelerometer, which sends a signal to the logic circuit 126. The desired programming is achieved through a particular sequence of shakes or taps.

Another example involves providing the inhalation device 10 with an input device in the form of a programming port that is configured to receive a cable, wire or the like for connecting the inhalation device 10 to an external device, such as a computer. The programming port is electrically connected to the logic circuit 126 so that programming instructions can be provided to the logic circuit 126 via the external device. The programming port could also be used to download data from the inhalation device 10 and recharge the power source 42. A further example uses an input device in the form of a radio frequency (RF) or other type of wireless receiver disposed inside of the inhalation device 10 and electrically connected to the logic circuit 126. The user would then use an external device with compatible wireless capability to wirelessly transmit programming instructions to the inhalation device 10. It is also possible to use magnetic induction to provide programming instructions. This would involve a first element, such as a coil, disposed inside of the inhalation device 10 and electrically connected to the logic circuit 126, and a second element, such as a magnet, located externally of the inhalation device 10. Waving the magnet over the coil would produce a temporary electric current in the coil, sending a signal to the logic circuit 126. The desired programming is achieved by waving the magnet over the coil in a particular sequence.

Another example uses the indicator light 20 as an input device. This is accomplished by using a bi-directional light-emitting diode (LED) as the light source 86. Bi-directional LEDs, such as the LED-based sensors proposed by Mitsubishi Electric Research Laboratories (see, for example, the web site at http://www.merl.com/projects/LED_chemical_sensors/), function as a light emitter when driven in forward bias and as a light detector when driven in reverse bias. When functioning as a light detector, the bi-directional LED will produce a signal in response to a flash of light impinging thereon, which signal is transmitted to the logic circuit 126. The desired programming can be achieved by providing a particular sequence of flashes. A bi-directional LED is also capable of functioning as the light source 86.

In another example, programming of the control electronics can be accomplished through the cartridge 16. In this instance, multiple interchangeable cartridges 16 are provided, and each cartridge has an input device, such as a memory chip or logic circuit containing particular programming instructions, mounted therein. Different cartridges 16 would provide different programming instructions. The cartridge input device makes an electrical connection with the logic circuit 126 when its cartridge 16 is connected to the atomizing unit 14 of an assembled inhalation device 10. The programming of the inhalation device 10 can thus be changed by installing a different cartridge 16. That is, the desired programming is achieved by installing the cartridge 16 having the appropriate programming instructions. This type of component programming could also be accomplished by providing a number of interchangeable atomizing units 14 having input devices with different programming instructions, instead of using interchangeable cartridges 16.

In one operating mode, the control electronics meter (i.e., supply in a measured or regulated amount) the deliverables discharged with the vapor through the orifice 18. The amount of deliverables contained in a puff is also referred to herein as the dose or dosage. The metering can include controlling the maximum amount of deliverables (i.e., the maximum dosage) discharged with a single puff, controlling the maximum number of doses discharged during a set period of time, or both.

In one embodiment, the logic circuit 126 controls the on-time of the atomizing device 108 to meter the maximum dosage delivered by a single puff. As described above, the control electronics activate the atomizing device 108 when the pressure transducer 38 is triggered by a user drawing on the inhalation device 10. While activated, the atomizing device 108 atomizes media on the wick 114, creating a vapor containing the deliverable from the medium. The logic circuit 126 deactivates the atomizing device 108 after a predetermined period of time, even if the user draws on the inhalation device 10 for a longer time. The atomizing device 108 ceases to atomize media upon being deactivated. Therefore, the amount of media atomized during a single puff, and thus the maximum dosage in the puff, is limited by the predetermined on-time of the atomizing device 108. The duration of the on-time of the atomizing device 108 dictates the maximum possible dosage in a puff regardless of how long air is drawn through the inhalation device 10 during the puff. A dosage smaller than the maximum dosage is possible by drawing on the inhalation device 10 for a time shorter than the predetermined on-time, but the maximum dosage cannot be exceeded.

Where the atomizing device 108 is a heating coil, it is possible to meter the maximum dosage delivered by a single puff based on temperature rather than time. In this case, a sensor for sensing the temperature in the atomization chamber 104 is electrically connected to the logic circuit 126. When the atomizing device 108 is activated as the user draws on the inhalation device 10, media is heated and atomized, creating a vapor containing the deliverables from the medium. If the temperature in the atomization chamber 104 exceeds a predetermined value, the logic circuit 126 deactivates the atomizing device 108 even if the user continues to draw on the inhalation device 10, thereby limiting the maximum dosage of the puff.

There are also multiple approaches for the logic circuit 126 to meter the maximum number of doses discharged during a set period of time. For instance, the logic circuit 126 can control a minimum time interval between activations of the atomizing device 108. That is, after the logic circuit 126 activates the atomizing device 108 in response to the user puffing on the inhalation device 10, the logic circuit 126 will not activate the atomizing device 108 again until a predetermined period of time (the minimum time interval) has elapsed. If the user puffs again on the inhalation device 10, and thereby triggers the pressure transducer 38, before the minimum time interval has elapsed, the logic circuit 126 will not activate atomizing device 108. The minimum time interval can be set by the user via one or more of the input devices 124.

Another possible approach is to control the number of atomizing device activations permitted during a set period of time. For example, the logic circuit 126 could be programmed to activate the atomizing device 108 no more than five times during a 30 minute period. A cycle begins when a user first takes a puff on the inhalation device 10 after an extended period of inactivity, thereby activating the atomizing device 108. The clock 122, functioning as a timer, begins tracking elapsed time. If the user takes four more puffs (for a total of five puffs) before 30 minutes elapse, then the logic circuit 126 will not activate the atomizing device 108 for the remainder of the 30-minute period, even if the user takes further puffs on the inhalation device 10. After 30 minutes, the timer is reset and the logic circuit 126 will again permit activation of the atomizing device 108. The cycle would restart upon the next puff by the user. A maximum of five puffs over a 30 minute period is given by example only; any number of puffs and any period of time could be utilized. The maximum number of permitted activations and the length of the set period of time can be changed by programming the logic circuit 126.

Yet another approach would be to use the clock 122 to track cumulative on-time of the atomizing device 108. When the cumulative on-time of the atomizing device 108 reaches a predetermined value (through one or more puffs), then the atomizing device 108 would be turned off (i.e., not activated even if the user puffs on the inhalation device 10 and triggers the pressure transducer 38) for a predetermined period of time. That is, the logic circuit 126 would not activate the atomizing device 108 even if the user puffs on the inhalation device 10 during the predetermined period of time. Once the predetermined period of time elapses, the cumulative on-time is reset to zero and the logic circuit 126 again allows the atomizing device 108 to be activated.

The user can re-program the control electronics using one or more of the input devices 124 to change the maximum dosage discharged with a single puff and/or the maximum number of doses that can be discharged during a set period of time. The metering programming can be based on factors such as the type of deliverable being used (i.e., different metering depending on the deliverable). In some instances, the metering programming is simply a matter of the user's individual preferences. That is, the user can program whatever maximum dosage and number of dosage he or she desires. In other instances, at least with respect to certain deliverables, the user's ability to change or program the metering can be restricted based on regulatory limits. For instance, the Food and Drug Administration or other agencies may place limits on the maximum possible dosage for deliverables such as nicotine and THC. In this case, the control electronics would be configured so that it would be impossible to program the device to exceed such limits.

As mentioned above, the inhalation device 10 has output devices (e.g., the indicator light 20, the display 22, and the audio signal device 128) for providing feedback to the user. By illuminating when the user puffs on the inhalation device 10, the indicator light 20 indicates operation of the inhalation device 10. This indication can be supplemented by the audio signal device 128 emitting a sound when the user puffs on the inhalation device 10. The audio signal device 128 could also produce another audio signal when the inhalation device 10 is not being used properly. The indicator light 20 can also be used to indicate power remaining status. For instance, if the power level of the power source 42 falls below a predetermined threshold level, then the logic circuit 126 can cause the indicator light 20 to flash repeatedly to provide an indication of the low power level. The display 22 could also be used to provide a low battery warning, either in addition to, or instead of, the indicator light 20.

The indicator light 20 can be a single color or multi-color light. If multi-color, the indicator light 20 can be operated so as to produce a different color depending on the deliverable of the medium in the cartridge 16. For example, the light 20 could be blue for nicotine, brown for caffeine, green for THC, orange for medications, and so on. These color indications could also be supplemented by unique sounds emitted from the audio signal device 128 depending on the deliverable.

The display 22 can utilize any suitable display technology, including but not limited to LED, LCD and E Ink. The display 22 can cover only a portion of the electronics section housing 24, as shown in the FIGS. 1 and 2, or it can cover the entire outer surface of the electronics section housing 24. The display 22 is useful for displaying a variety of information to the user. Types of information that can be displayed include instructions for using the inhalation device 10, the type of deliverable being used, the number of remaining doses under the metering regimen, the current count of dosages; the time out period, and other metering feedback. The display 22 can also show logos and/or decorations, which can be changeable.

The control electronics can also be programmed to retain device operation information for later download over a synchronization channel. The type of data collected could include puffs per day, puffs per minute, cartridges used, average dosage, etc. The collected data would typically be stored in the memory 120 and can be downloaded in any suitable manner. For instance, if the inhalation device 10 is provided with a programming port as described above, this port could be utilized to connect the inhalation device 10 to a computer with a USB cable or the like and download the data to the computer. The data alternatively could be downloaded wirelessly. The data download would allow users to analyze their usage of the inhalation device 10. This could be helpful for users who are using nicotine in the inhalation device 10 and trying to quit traditional smoking by allowing them to track their nicotine use and their progress.

The control electronics can provide operating modes other than the metering mode. For instance, the inhalation device 10 could have a party mode in which the indicator light 20 illuminates in different patterns, such as blinking or static. This could also involve a multi-color light that randomly changes color, either continuously or with each puff on the inhalation device 10. The light could also change colors slowly; for example, the light could be red, then slowly change to orange, then slowly change to purple, then to blue, green and so on. A party mode could also involve varying audio outputs from the audio signal device 128 and varying decorations or logos shown on the display 22.

Another possibility is a military mode. In this mode, the control electronics disable the indicator light 20 and the audio signal device 128 so that use of the inhalation device 10 in the field will not give away the soldier's position. The control electronics also randomly vary device operation times to suppress the RF signature of the inhalation device 10. The dosing can also be changed based on mission parameters, e.g., caffeine delivery for military usage. The display 22 (particularly where it covers the entire outer surface of the electronics section housing 24) can be caused to display a camouflage design.

A marketing mode can be provided for displaying inhalation devices at retail shops or the like. This could include programmed demonstrations and other unattended attraction features. For instance, the vaporizer 10 could provide various light displays or a scrolling message on the display 22.

Other possible modes include a cooperative mode which permits device interactivity, such as an RF interface to a mobile phone, and a lock off mode in which the vaporizer 10 is turned off for security (i.e., to prevent unauthorized use) or to save battery power during shipment or other extended periods on non-use. The vaporizer 10 can also have various "key" encryption means to prevent use of unauthorized deliverables in the device. This could be accompanied by feedback such as disabling the atomizing unit 14, flashing the indicator light 20, an audio signal from device 128, or a display on the display 22. The vaporizer 10 could also have an administration mode in which an administrator would be enabled to adjust, update or delete any operations. An authorized user mode is also possible. This would be similar to the administration mode but without as many privileges. It is possible that any of the operating modes could be run independently, or a combination of modes could be run together and prioritized by the control electronics.

The control electronics can also dictate operational parameters to protect the vaporizer 10 and the user. For instance, the control electronics can control operation to prevent overheating of the medium and/or the atomizing unit 14, adjust for maximum battery life, and adjust for charging time. Feedback parameters for providing warnings such as low battery or imminent overheating as also provided.

While specific embodiments of the present invention have been described, it should be noted that various modifications thereto can be made without departing from the spirit and scope of the invention as defined in the appended claims.

What is claimed is:

1. A personal inhalation device comprising:
   an outer shell having an orifice formed therein and containing a medium having one or more deliverables;
   an atomizing unit disposed within said shell, whereby said atomizing unit heats air flowing thereon, and the heated air atomizes said medium creating a vapor containing said deliverables when a user puffs on said orifice such that said vapor containing said deliverables is discharged through said orifice;
   control electronics for controlling operation of said personal inhalation device, wherein said control electronics meter the deliverables discharged with said vapor;
   an input device providing a user interface for selectively programming said control electronics to change at least one of a plurality of unique operating parameters of the personal inhalation device; and
   an indicator light;
   wherein said indicator light is an assembly comprising:
      a translucent base member mounted in one end of said outer shell, said base member having a socket formed therein,
      a translucent lens member having a body portion defining an outer surface,
      a first connector extending from one end of said body portion,
      a second connector extending from another end of said body portion, said first connector being inserted into said socket,
      a tip member mounted on said second connector, and
      a light source mounted on said base member, said light source illuminating said outer surface of said body portion when activated; and
   wherein the input device comprises at least one device selected from the group consisting of a pin configured to define at least one of the unique operating parameters, and a pressure transducer triggered by a sequence of activities selected from the group consisting of a plurality of inhalations, a plurality of exhalations, a combination thereof, a plurality of tappings on the personal inhalation device, and a plurality of tappings of the personal inhalation device against a surface, the pressure transducer configured to define at least one of the unique operating parameters.

2. The personal inhalation device of claim 1 wherein said control electronics control the maximum amount of deliverables discharged during a single puff and the maximum number of deliverable doses discharged during a set period of time.

3. The personal inhalation device of claim 1 wherein said light source is a bi-directional light-emitting diode.

4. The personal inhalation device of claim 1 wherein said control electronics can be programmed to disable said light source.

5. The personal inhalation device of claim 1 further comprising a multi-color indicator light that produces a different color depending on the deliverable contained in said outer shell.

6. The personal inhalation device of claim 1 further comprising a display for outputting information about said personal inhalation device.

7. The personal inhalation device of claim 1 further comprising an audio signal device for outputting information about said personal inhalation device.

8. The personal inhalation device of claim 1 wherein said control electronics are programmed to retain operation information and further comprising means for downloading said operation information.

9. The personal inhalation device of claim 1 wherein the operating parameters comprise at least one of a maximum amount of deliverables discharged during a single puff, a maximum amount of deliverable doses discharged during a set period of time and a combination thereof.

10. The personal inhalation device of claim 1 wherein said control electronics control the maximum amount of deliverables discharged during a single puff.

11. The personal inhalation device of claim 10 wherein said control electronics control the maximum amount of deliverables discharged during a single puff by controlling the on-time of said atomizing unit.

12. The personal inhalation device of claim 10 wherein said control electronics control the maximum amount of deliverables discharged during a single puff based on temperature in said atomizing unit.

13. The personal inhalation device of claim 10 wherein the input device provides a user interface for selectively programming said control electronics to change the maximum amount of deliverables discharged during a single puff.

14. The personal inhalation device of claim 1 wherein said control electronics control the maximum number of deliverable doses discharged during a set period of time.

15. The personal inhalation device of claim 14 wherein said control electronics control the maximum number of deliverable doses discharged during a set period of time by controlling a minimum time interval between activations of said atomizing unit.

16. The personal inhalation device of claim 14 wherein said control electronics control the maximum number of deliverable doses discharged during a set period of time by controlling the number of activations of said atomizing unit permitted during said set period of time.

17. The personal inhalation device of claim 14 wherein said control electronics control the maximum number of deliverable doses discharged during a set period of time based on the cumulative on-time of said atomizing unit.

18. The personal inhalation device of claim 14 further comprising means for programming said control electronics to change the maximum number of deliverable doses discharged during a set period of time.

* * * * *